(12) United States Patent
Murray

(10) Patent No.: US 6,831,187 B2
(45) Date of Patent: Dec. 14, 2004

(54) MULTIMETALLIC CATALYST COMPOSITIONS FOR THE POLYMERIZATION OF OLEFINS

(75) Inventor: Rex Eugene Murray, Cross Lanes, WV (US)

(73) Assignee: Univation Technologies, LLC, Houston, TX (US)

( * ) Notice: Subject to any disclaimer, the term of this patent is extended or adjusted under 35 U.S.C. 154(b) by 391 days.

(21) Appl. No.: 10/022,997

(22) Filed: Dec. 18, 2001

(65) Prior Publication Data

US 2004/0054150 A1 Mar. 18, 2004

(51) Int. Cl.$^7$ .............................. C07F 7/00; C07F 9/00; B01J 31/00
(52) U.S. Cl. ............................. 556/51; 556/52; 556/57; 556/58; 556/45; 556/46; 556/42; 556/43; 556/137; 556/11; 556/28; 502/103; 502/152
(58) Field of Search .............................. 556/51, 52, 42, 556/43, 57, 58, 46, 45, 137, 11, 28; 502/103, 152

(56) References Cited

U.S. PATENT DOCUMENTS

| | | | |
|---|---|---|---|
| 6,096,676 A | 8/2000 | Murray | 502/117 |
| 6,103,657 A | 8/2000 | Murray | 502/155 |

FOREIGN PATENT DOCUMENTS

| | | |
|---|---|---|
| DE | 42 02 889 A1 | 8/1993 |
| EP | 0 320 169 A2 | 6/1989 |
| EP | 0 509 233 A2 | 10/1992 |
| EP | 0 349 886 B1 | 9/1995 |
| EP | 0 761 694 B1 | 3/1997 |
| EP | 0 803 520 A1 | 10/1997 |
| WO | WO 92/12162 | 7/1992 |
| WO | WO 96/23010 | 8/1996 |
| WO | WO 96/23101 | 8/1996 |
| WO | WO 96/33202 | 10/1996 |
| WO | WO 97/02298 | 1/1997 |
| WO | WO 97/45434 | 12/1997 |

OTHER PUBLICATIONS

Gibson et al., "Synthesis and structural characterisation of aluminum imino–amide and pyridyl–amide complexes: bulky monoanionic N,N chelate ligands via methyl group transfer" Journal of Organometallic Chemistry 550, (1998) 453–456.

Fuhrmann et al., "Octahedral Group 4 Metal Complexes That Contain Amine, Amido, and Aminopyridinato Ligands: Synthesis, Structure, and Application in α–Olefin Oligo– and Polymerization" Inorg. Chem 1996, 35, 6742–6745 (Feb.).

George J.P. Briotovsek et al., "Novel Olefin Polymerization Catalysts Based on Iron and Cobalt" Chem. Commun., 1998 849–850 (May).

Deelman et al., "Lithium Derivatives of Novel Monoaniomic Di–N,N'–chelating Pyridyl– and Quinolyl–I–azaallyl Ligands" Organometalics 1997, 16, 1247–1252 (Aug.).

Deelman et al., "Novel monanionic di–N,N'–centered chelating ligands and the $C_1$ and $C_2$ symmetrical zirconium complexes" Journal of Organometallic Chemistry 513 (1996) 281–285 (Nov.).

Hitchcock et al., "Transformation of the Bis(trimethylsilyl) methyl into Aza–allyl and β–Diketinimato Ligands; the X–Ray Structures of $[Li \{N(R)C(Bu')CH(R)\}]_2$ and $[Zr\{N(R)C(Bu')CHC(Ph)N(R)\}Cl_3](R=SiMe_3)$" J. Chem. Soc., Chem. Commun. (1994) 2637–2638 (Aug.).

Hitchcock et al., "Transformaton of the Bis(trimethylsilyl) methyl into a β–Diketinimato Ligand; the X–Ray Structure of $[Li(L'L')]_2$, $SnCi(Me)_2$ $(L'L')$ and $SnCi(Me)_2$ $(LL)$, $(L'L'=N(R)C(Ph)C(H)C(Ph)NR,LL=N)H)C(Ph)NH$, $R—SiMe_3$)" J. Chem. Soc., Chem. Commun. (1994) 1699–1700 (May).

Clarke, et al., Structural Investigations of the Dipyromethene Complexes of Calcium(II), Nickel(II) and Copper(II) Inorganica Chimica Acta. 166 (1989) 221–231 (Jun.).

Tjaden et al. "Synthesis, Structures, and Reactivity of $(R_6$–$acen)ZrR'_2$ and $(R_6$–$acen)Zr (R')^+$ Complexes (R=H, F; R'=CH_2CMe_3, CH_2Ph)$" Organometallics 1995, 14, 371–386 (Jul.).

Corazza et al., cis–and trans–Dichloro–derivatives of Six– and Seven–co ordinate Zirconium and Hafnium bonded to Quadridentate Schiff–base Ligands. Crystal Structures of $[Zr(acen)Cl_2(thf)]$, $[M(salphen)Cl_2(thf)]0.5thf$, $[M(acen)Cl_2$, $(M=Zr$ or $Hf)$, and $[Zr(msal)Cl_2]$ acen=N,N'=ethylenebis(acetylacetoneiminate), salphen=N, N'–o–phenylenebis(salicylideneiminate), msal= N–methylsalicylideneiminate, and thf=tetrahydrofuran] J. Chem. Soc. Dalton Trans. (1990) 1335–1344 (Aug.).

Cozzi et al., "Oxazoline Early Transiton Metal Complexes: Functionalizable Achiral Titanium(IV), Titanium(III), Zirconium(IV), Vanadium(III), and Chiral Zirconium(IV) Bis(oxazoline) complexes" Inorg. Chem (1995), 34, 2921–2930, (Dec.).

Korine et al., "Bis(Trimethylsilyl)benzamidinate zirconium dichlorides. Active catalysts for ethylene polymerization" Journal of Organometallic Chemistry 503 (1995) 307–314 (Mar.).

(List continued on next page.)

Primary Examiner—Porfirio Nazario-Gonzalez
(74) Attorney, Agent, or Firm—Lisa Kimes Jones; Kevin M. Faulkner

(57) ABSTRACT

The present invention relates to novel hetero-multimetallic catalyst precursors and catalysts for the polymerization of olefins.

30 Claims, 1 Drawing Sheet

OTHER PUBLICATIONS

Gomez et al., "*Mono–η–cyclopendtadienyl–benzamidinato chloro compounds of titanium, zirconium and hafnium*" Journal of Organometallic Chemistry 491 (1995) 153–158 (Aug.).

Flores, et al., "[*N,N'–Bis(trimethylsilyl)benzamidinato*] *titanium and–zirconium Compounds. Synthesis and Application as Precursors for the Syndiospecific Polymerization of Styrene*" Organometallics 1995, 14, 1827–1833 (Oct.).

Dias et al., "*N–Methyl–2(methylamino)troponiminate Complexes of Tin(II), Gallium(III), and Indium(III). Syntheses of [(ME)$_2$ATI]$_2$GaI and [(Me)$_2$ATI]$_2$InCl Using the Tin(III) Reagent [(Me)$_2$ATI[$_2$Sn*" Inorg. Chem. 1996, 35, 6546, 35, 6546–6551 (Jun.).

Cotton et al., "*Structural Studies of formamidine compounds: from neutral to anionic and cationic species*" Polyhedron vol. 16 No. 3 pp. 541–550, 1997 (Apr.).

Gornitzka et al., "*Coordinationo of the Bis(pyridyl)methyl Substituent to Group 1 and 13 Metals*" Organometallics 1994, 13, 4398–4405 (May).

Roesky et al., "*Benzamidnatokomplexe mit Haupt– and Nebengruppen–Elementen—Strukturen von PhC(NSiMe$_3$)$_2$TiCl$_2$ and PhC(NSiMe$_3$)$_2$MoO$_2$*" Chem. Ber 121, 1403–1406 (1988) (Feb.).

Cloke et al., "*Zirconium Complexes incorporating the New Tridentate Diamide Ligand [(Me$_3$Si)N{CH$_2$CH$_2$N(SiMe$_3$)}$_2$]$^{2-}$(L); the Crystal Structures of [Zr(BH$_4$)$_2$L]and [ZrCl{CH(SiMe$_3$)$_2$}L]*" J. Chem Soc. Dalton Trans 1995 25–30 (Jul.).

Linden et al., "*Polymerization of α–Olefins and Butadiene and Catalytic Cyclotrimerization of 1–Alkynes by a New Class of Group IV Catalysts. Control of Molecular Weight and Polymer Microstructure via Ligand Turning in Sterically Hindered Chelating Phenoxide Titanium and Zirconium Species*" J. Am.Chem. Soc. 1995, 117, 3008–3021 (Jul).

Brand et al. "*Facile Reduction of a Dialkyl Zirconium(IV) Octaethylporphyrin (OEP) Complex by H$_2$: Crystal Structure and Spectroscopic Characterization of [(OEP)ZrCH$_2$SiMe$_3$]*" Angew. Chem. Int. Ed. Engl. 1994 33, No. 1 95–97 (Jul.).

Solari et al., "*Functionalizedable 5,5,10,10,15,15,20,20–Octaethylporphyrinogen Complexes of Early Transition Metals: Synthesis and Crystal Structure of Titanium–, Vanadium– and Chromium– (III) Derivatives and a Two–electron Oxidation of the Porphyrinogen Skeleton*" J. Chem. Soc. Dalton Trans 1994 2015–2017 (Apr.).

Uhrhammer et al., "*Cationic d$^0$ Metal Alkyls Incorporating Tetraaza–Macrocycle Ancillary Ligands. Synthesis and Reactivity of (Me$_8$taa)M(R)$^+$ and (Me$_4$taen)M(R)$^+$(M=Zr, Hf) Complexes*" J. Am. Chem. Soc. 1993, 115, 8493–8494 (Apr.).

Giannini, et al., "*Tetraaza[14]annulenezirconium (iv) Complexes with Butadiene Ligands and their Relationship with Bis(cyclopentadienyl)zirconium(IV) Complexes.*" Angew. Chem. Int. Ed. Engl. 1994, 33 No. 21 (May).

Kol, et al., "*Synthesis of Molybdenum and Tungsten Complexes That Contain Triamidoamine Ligands of the Type (C$_6$F$_5$NCH$_2$CH$_2$)$_3$N and Activation of Dinitrogen by Molybdenum*" J. Am. Chem. Soc. 1994, 116, 4382–4390, (Oct.).

Bei et al., "*Synthesis, Structures, Bonding, and Ethylene Reactivity of Group 4 Metal Alkyl Complexes Incorporating 8–Quinolinolato Ligands*" Organometallics 1997, 16, 3282–3302 (Mar.).

Tsukahara, et al., "*Neutral and Cationic Zirconium Benzyl Complexes Containing Bidentate Pyridine–Alkoxide Ligands. Synthesis and Olefin Polymerization Chemistry of (pyCR$_2$O)$_2$Zr(CH$_2$Ph)$_3$ and (pyCR$_2$O)$_2$Zr(CH$_2$Ph)$^+$ Complexes*" Organometallics 1997, 16, 3303–3313 (Mar.).

Kim et al., "*Synthesis, Structures, Dynamics, and Olefin Polymerization Behavior of Group 4 Metal (pyCAr$_2$O)$_2$M(NR$_2$)$_2$ Complexes Containing Bidentate Pyridine–Alkoxide Ancillary Ligands*" Organometallics 1997, 16, 3314–3323 (Mar.).

Durfee et al., "*Formation and Characterization of η$^2$–Imine and η$^2$–Azobenzene Derivatives of Titanium Containing Ancillary Aryloxide Ligation*" Organometallics, vol. 9, No. 1, 1990, pp 75–80, (Jan.).

Lappert et al., "*Recent studies on metal and metalloid bid(trimethylsilyl) methyls and the transformation of the bis(trimethylsilyl)methyl into the azaallyl and β–diketinimato ligands*" Journal of Organometallic Chemistry 500, (1995) 203–217, (Sep.).

FIGURE
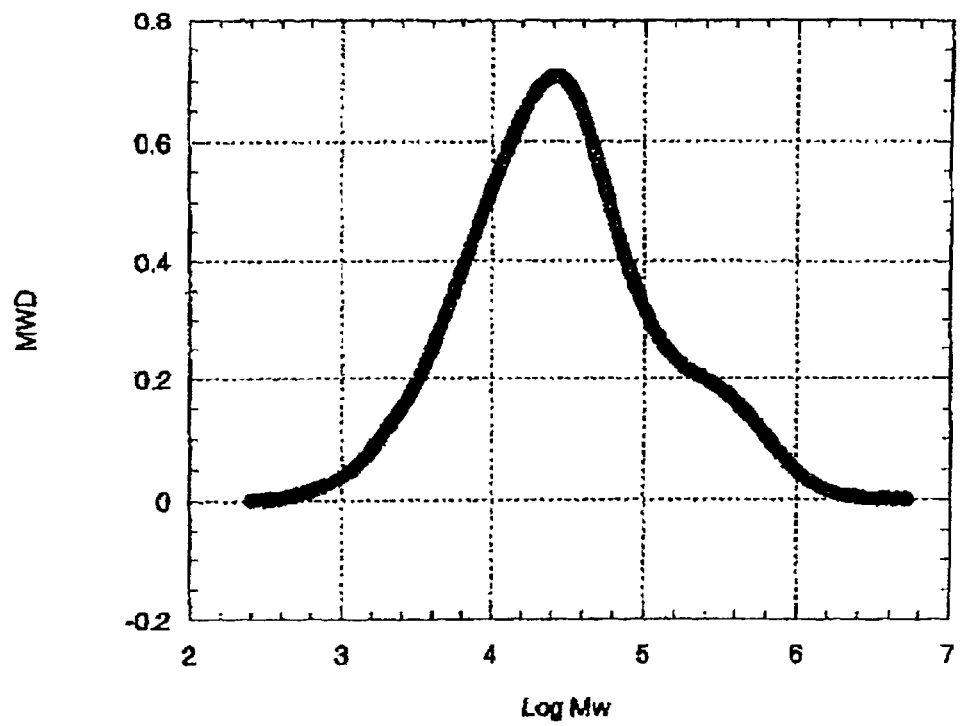

MULTIMETALLIC CATALYST COMPOSITIONS FOR THE POLYMERIZATION OF OLEFINS

FIELD OF THE INVENTION

The present invention relates to a family of novel multimetallic catalyst precursors and catalysts for use in the polymerization of olefins.

BACKGROUND OF THE INVENTION

A variety of metallocenes and other single site-like catalysts have been developed to produce olefin polymers. Metallocenes are organometallic coordination complexes containing one or more pi-bonded moieties (i.e., cyclopentadienyl groups) in association with a metal atom. Catalyst compositions containing metallocenes and other single site-like catalysts are highly useful in the preparation of polyolefins, producing relatively homogeneous copolymers at excellent polymerization rates while allowing one to tailor closely the final properties of the polymer as desired.

Recently, work relating to certain nitrogen-containing, single site-like catalyst precursors has been published. PCT Application No. WO 96/23101 relates to di(imine) metal complexes that are transition metal complexes of bidentate ligands selected from the group consisting of:

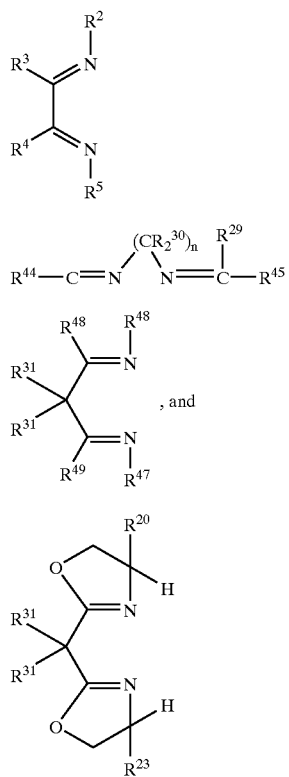

wherein said transition metal is selected from the group consisting of Ti, Zr, Sc, V, Cr, a rare earth metal, Fe, Co, Ni, and Pd;

$R^2$ and $R^5$ are each independently hydrocarbyl or substituted hydrocarbyl, provided that the carbon atom bound to the imino nitrogen atom has at least two carbon atoms bound to it;

$R^3$ and $R^4$ are each independently, hydrogen, hydrocarbyl, substituted hydrocarbyl, or $R^3$ and $R^4$ taken together are hydrocarbylene or substituted hydrocarbylene to form a carbocyclic ring;

$R^{44}$ is a hydrocarbyl or substituted hydrocarbyl, and $R^{28}$ is hydrogen, hydrocarbyl or substituted hydrocarbyl or $R^{44}$ and $R^{28}$ taken together form a ring;

$R^{45}$ is a hydrocarbyl or substituted hydrocarbyl, and $R^{29}$ is hydrogen, hydrocarbyl or substituted hydrocarbyl or $R^{45}$ and $R^{29}$ taken together form a ring;

each $R^{30}$ is independently hydrogen, hydrocarbyl or substituted hydrocarbyl, or two of $R^{30}$ taken together form a ring;

each $R^{31}$ is independently hydrogen, hydrocarbyl or substituted hydrocarbyl;

$R^{46}$ and $R^{47}$ are each independently hydrocarbyl or substituted hydrocarbyl, provided that the carbon atom bound to the imino nitrogen atom has at least two carbon atoms bound to it;

$R^{48}$ and $R^{49}$ are each independently hydrogen, hydrocarbyl, or substituted hydrocarbyl;

$R^{20}$ and $R^{23}$ are each independently hydrocarbyl, or substituted hydrocarbyl;

$R^{21}$ and $R^{22}$ are independently hydrogen, hydrocarbyl, or substituted hydrocarbyl; and n is 2 or 3;

and provided that:

the transition metal also has bonded to it a ligand that may be displaced by or added to the olefin monomer being polymerized; and when the transition metal is Pd, said bidentate ligand is (V), (VII) or (VIII).

Similarly, PCT Application No. WO 97/02298, which is incorporated herein by reference, relates to a process for the polymerization of olefins, comprising contacting a polymerizable monomer consisting of ethylene, a norbornene or a styrene, with a catalyst system comprising the product of mixing in solution a zerovalent tricoordinate or tetracoordinate nickel compound that has at least one labile ligand, wherein all ligands are neutral, an acid of the formula HX, and a first compound selected from a group listed therein.

Also, PCT Application No. WO 96/33202, which is also incorporated herein by reference, relates to a transition metal catalyst containing pyridine or quinoline moiety having the formula:

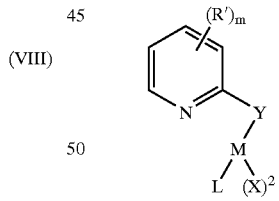

wherein Y is O, S, NR,

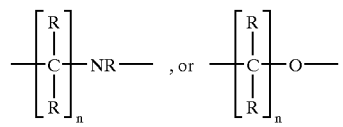

wherein each R is independently selected from hydrogen or $C_1$ to $C_6$ alkyl, each R' is independently selected from $C_1$ to $C_6$ alkyl, $C_1$ to $C_6$ alkoxy, $C_6$ to $C_{16}$ aryl, halogen, or $CF_3$, M is titanium, zirconium, or hafnium, each X is independently selected from halogen, $C_1$ to $C_{16}$ alkyl, $C_1$ to $C_6$ alkoxy, or

L is X, cyclopentadienyl, $C_1$ to $C_6$ alkyl substituted cyclopentadienyl, indenyl, fluroenyl, or

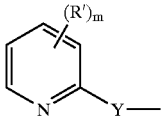

wherein m is 0 to 4, and n is 1 to 4.

Similarly, Fuhrmann et al., *Inorg. Chem.* 35:6742–6745 (1996) discloses certain Group 4 metal complexes containing amine, amido, and aminopyridinato ligands such as:

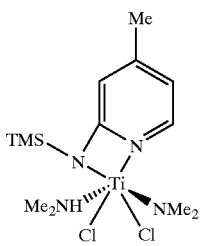

wherein TMS is trimethylsilyl.

Also, U.S. Pat. No. 6,103,657, which is also incorporated herein by reference, teaches an olefin polymerization catalyst composition made from a heteroatom-containing precursor having the formula:

wherein each A is represented by the formula:

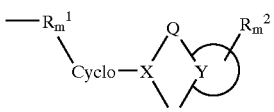

wherein M is a metal selected from the group consisting of Group 3 to 13 elements and Lanthanide series elements;
each L is a monovalent, bivalent, or trivalent anion;
X and Y are each heteroatoms;
Cyclo is a cyclic moiety;
each $R^1$ is independently a group containing 1 to 50 atoms selected from the group consisting of hydrogen and Groups 13 to 17 elements, and two or more adjacent $R^1$ groups may be joined to form a cyclic moiety;
each $R^2$ is independently a group containing 1 to 50 atoms selected from the group consisting of hydrogen and Group 13 to 17 elements, and two or more adjacent $R^2$ groups may be joined to form a cyclic moiety;
Q is a bridging group;
each m is independently an integer from 0 to 5;
n is an integer from 1 to 4;
q is 1 or 2 and when q is 2, the A groups are optionally connected by a bridging group.

In one embodiment the catalyst precursor is represented by:

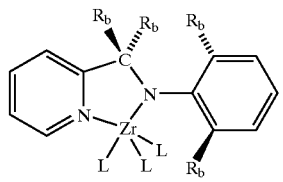

wherein $R_a$ and $R_b$ are each independently selected from the group consisting of alkyl, aryl, heterocyclic groups, and hydrogen and $R_a$ and $R_b$ can be optionally connected to form a ring; $R_c$ and $R_d$ are each independently selected from the group consisting of alkyl, aryl, and hydrogen; and each L is a monovalent anion.

Although there are a variety of single site catalysts taught in the prior art, some of which are commercially available, there still exist a need in the art for improved catalysts and catalyst precursors that are capable of producing polyolefins having predetermined properties.

SUMMARY OF THE INVENTION

In accordance with the present invention there is provided catalyst precursors represented by the formula:

wherein M is a metal selected from Groups 1 to 15 and the Lanthanide series of the Periodic Table of the Elements;
g is an integer equal to or greater than 1;
m is an integer equal to or greater than 2;
each L is a monovalent, bivalent, or trivalent anionic ligand;
p is an integer equal to or greater than 1;
n is an integer equal to or greater than 2;
G is a spacing group that is capable of bonding to at least two A substituents; and
at least one A is selected from the following catalytically active ligands:

Structures I

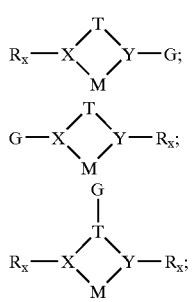

Structures II

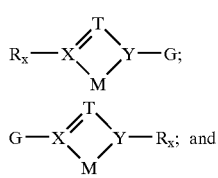

-continued

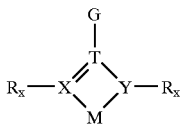

M is included for convenience to show that it is bound to atoms X and Y.

G is also included for convenience to show that it can be bound to atoms X, Y, or bridging group of atoms T.

T is a bridging group containing 2 or more bridging atoms.

R can be a non-bulky or a bulky subsitutent. If it is a non-bulky substituent it will have relatively low steric hindrance with respect to X or Y and is preferably a $C_1$ to $C_{20}$ alkyl group. R can also be a spacing group as defined herein for G.

If R is a bulky group it will have a relatively large steric hindrance with respect to X or Y and be selected from the group consisting of alkyl (preferably branched), alkenyl (preferably branched), cycloalkyl, heterocyclic (both heteroalkyl and heteroaryl), alkylaryl, arylalkyl, and polymeric.

k is an integer that will vary to satisfy the oxidation state of "X" and will range from about 1 to 3. For example, when X is phosphorous k will be an integer from 1 to 3, preferably 2 for Structures I and 1 for Structures II. When X is nitrogen k is equal to 2 for Structures I and 1 for Structures II and when X is sulfur k is an integer from 0 to 3.

G is included for convenience.

Two or more of X, R, T, Y and G; preferably X, R, T, and G can be independently co-joined by single, hybridize, or multiple bonds if desired.

BRIEF DESCRIPTION OF THE FIGURE

The sole FIGURE hereof is a plot of molecular weight distribution of the polyethylene product obtained using a catalyst prepared from reaction of zirconocene-Imine compound with tetrabenzyl zirconium as measured by size exclusive (gel permeation) chromatography showing evidence of bimodality distribution.

DETAILED DESCRIPTION OF THE INVENTION

As previously mentioned, the catalyst precursors of the present invention can be represented by the formula:

$$G_g A_n M_m L_p$$

wherein M is a metal from Groups 1 to 15, preferably from Groups 1 to 13, more preferably from Groups 3 to 7, and the Lanthanide series of the Periodic Table of the Elements. The Periodic Table of the Elements referred to herein is that table that appears in the inside front cover of Lange's Handbook of Chemistry, 15th Edition, 1999, McGraw Hill Handbooks.

g is equal to or greater than 1.

m is an integer equal to or greater than 2.

Each L is independently a neutral, a monovalent, bivalent, or trivalent anionic ligand; preferably containing from about 1 to 50 non-hydrogen atoms, more preferably containing from about 1 to 20 non-hydrogen atoms and is independently selected from halogen containing groups; alkyl; aryl; alkenyl; alkylaryl; arylalkyl; an $\eta^4$-diene,: hydrocarboxy; amides, phosphides; sulfides; silyalkyls; diketones; borohydrides; and carboxylates. More preferred are alkyl, arylalkyl, and halogen containing groups.

p is an integer equal to or greater than 1.

n is an integer equal to or greater than 2.

G is a spacing group that is capable of bonding to at least two A substituents. G will typically be: organic, including heteroaryl; inorganic; polymeric; or organometallic. G can also inherently possess one or more catalytically active sites. It is preferred that G be selected from alky, alkenyl, cycloalkyl, heterocyclic (both heteroalkyl and heteroaryl), alkylaryl, arylalkyl, and polymeric. It is also preferred that the G substituent contain from about 1 to 50, more preferably from about 1 to 20 non-hydrogen atoms. Also, one or more of the carbon or hydrogen positions may be substituted with an element other than carbon and hydrogen, preferably an element selected from Groups 14 to 17, more preferably a Group 14 element such as silicon, a Group 15 element such as nitrogen, a Group 16 element such as oxygen, or a Group 17 halogen. It will be understood that the spacing group G is bonded to either both Y or both X or one X and one Y for any given catalyst precursor. It will also be understood that G can be bonded to various combinations of X, Y, and T moieties.

When G is a polymeric group it is preferred that it be comprised of a polymer backbone containing at least two sites that will allow A substituents to become bonded pendent thereto.

At least one A is selected from the following catalytically active ligands:

Structures I

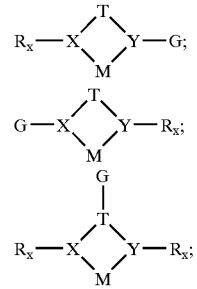

Structures II

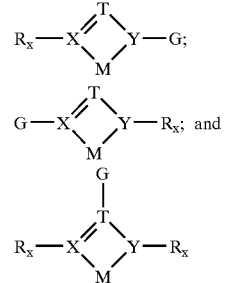

M is included for convenience to show that it is bound to atoms X and Y.

G is also included for convenience to show that it can be bound to atoms X and Y, or bridging group of atoms T.

Wherein T is a bridging group containing 2 or more, preferably 2 or 3 bridging atoms. T can also contain one or more elements selected from Groups 13 to 16. It is preferred that at least one bridging atom be a Group 14 element, preferably a carbon atom, and it is more preferred that all of the bridging atoms be carbon atoms. The total number of non-hydrogen atoms will be from about 2 to 50, preferably from about 2 to 20, and more preferably less than about 10.

The most preferred T groups are when there is a dimethyl group adjacent to X or Y.
Preferred bridging groups include:
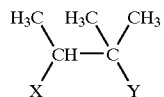 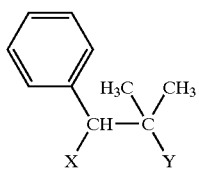
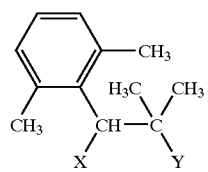 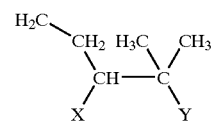
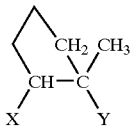
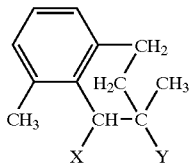
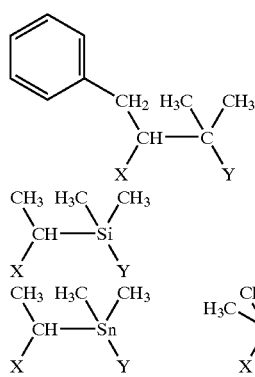 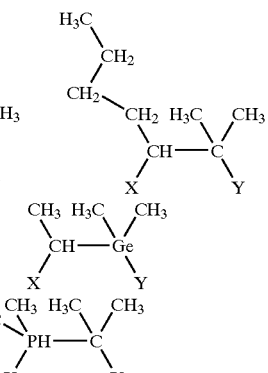
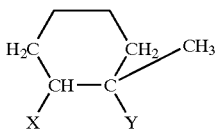
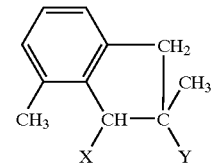
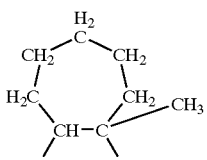 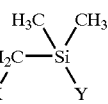
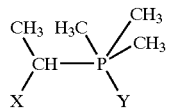 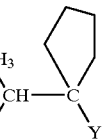
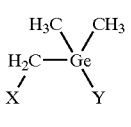 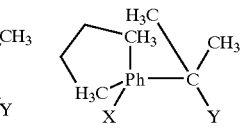
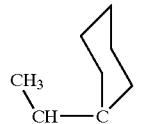 
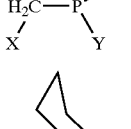 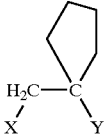
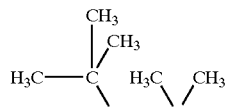 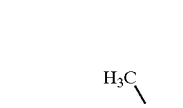
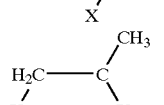 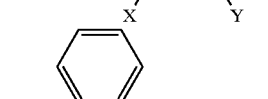
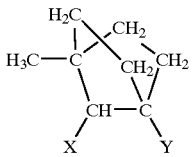 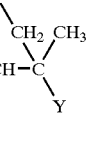
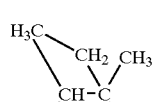 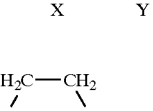
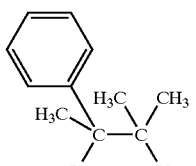 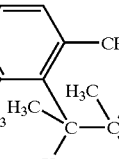
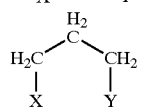 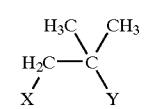
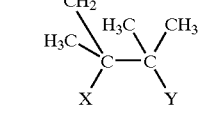 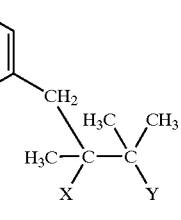

-continued
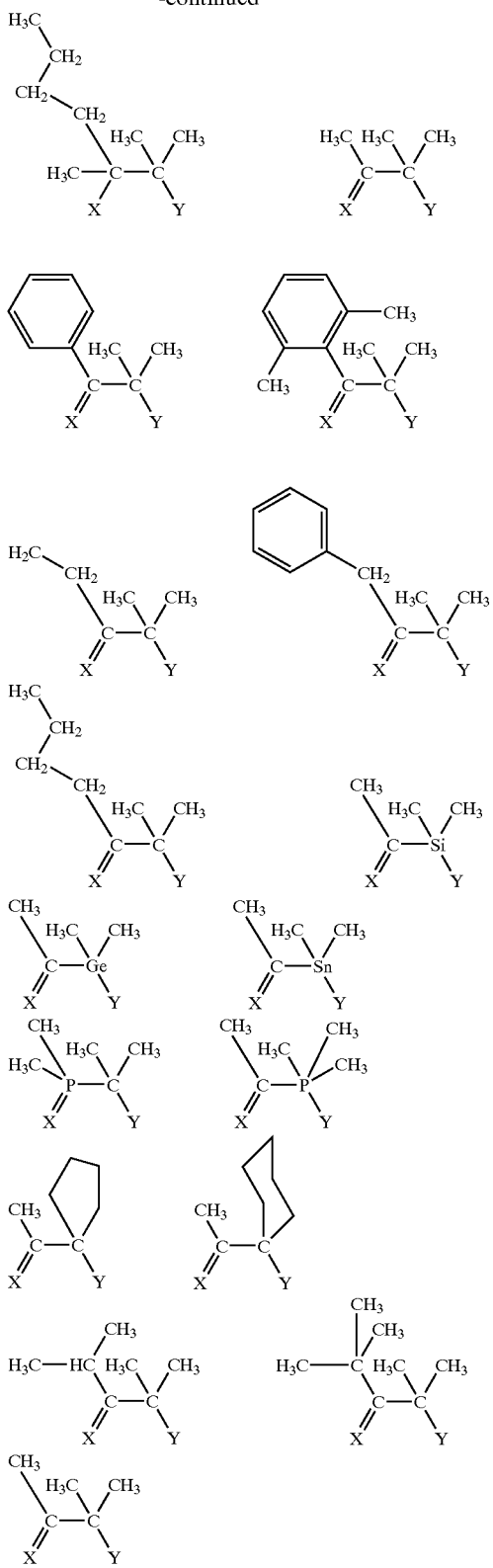
The X and Y substituents are included for convenience to show where the bridging groups would bridge. More preferred bridging groups are when only carbon atoms comprise the bridging atoms.
Non-limiting examples of G moieties suitable for use in the present invention include:
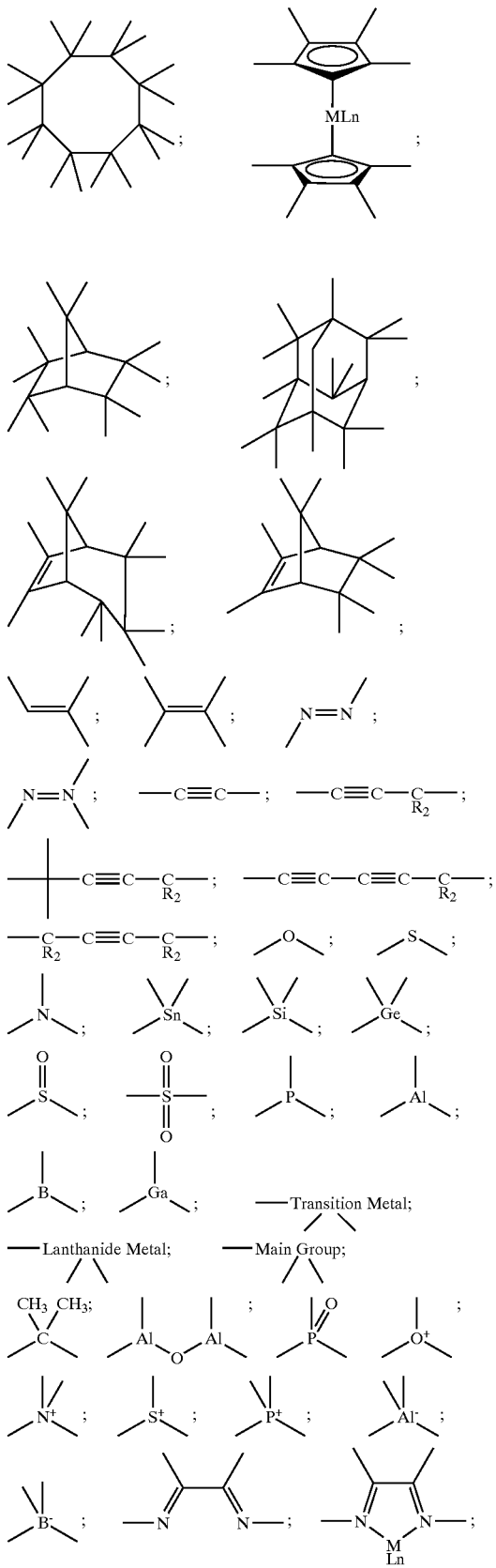

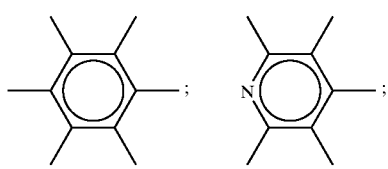
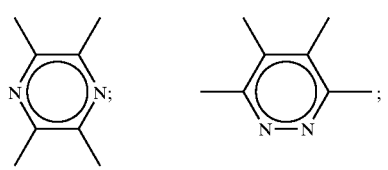
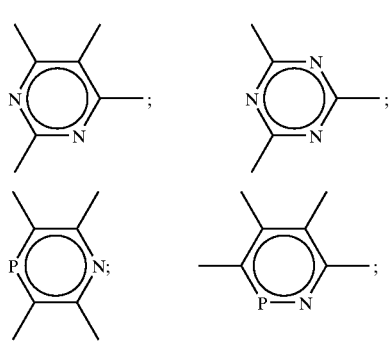

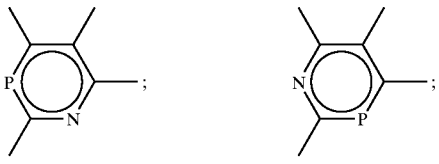
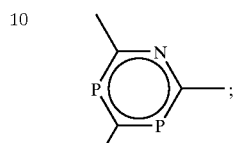
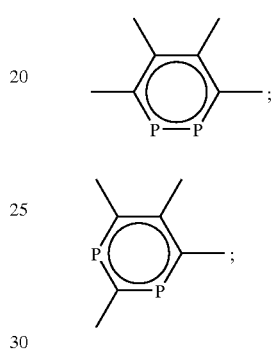

Spacing group G and also be selected from the following molecules that can be bonded to X, Y or bridging group T and any two or more suitable positions.

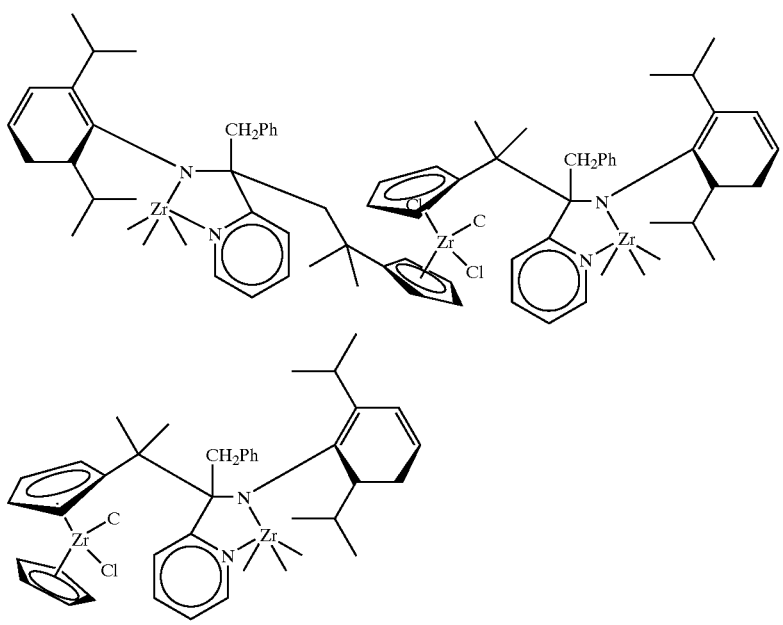

R can be a non-bulky subsitutent that has relatively low steric hindrance with respect to X or Y. Non-limiting examples of non-bulky substituents include straight and branched chain alkyl groups, preferably straight chain alkyl groups. R is also preferably a $C_1$ to $C_{30}$ alkyl group, more preferably a $C_1$ to $C_{20}$ alkyl group, and most preferably a primary alkyl group, such as an n-octyl group. If the non-bulky group is branched, the branch point must be at least 3 atoms removed from X or Y.

R can also be a bulky group that has a relatively large steric hindrance with respect to X or Y. That is, it can have branching within 3 atoms from X or Y. Such bulky groups can be selected from alkyl (preferably branched), alkenyl (preferably branched), cycloalkyl, heterocyclic (both heteroalkyl and heteroaryl), alkylaryl, arylalkyl, and polymeric, including inorganics such as the P-N ring structures set forth below and inorganic-organic hybrid structures, such as those set forth below. It is preferred that the R substituent contain from about 3 to 50, more preferably from about 3 to 30, most preferably about 2 to 20 non-hydrogen atoms. Also, one or more of the carbon or hydrogen positions may be substituted with an element other than carbon and hydrogen, preferably an element selected from Groups 14 to 17, more preferably a Group 14 element such as silicon, a group 15 element such as nitrogen, a Group 16 element such as oxygen, or a Group 17 halogen.

It is preferred that R be a $C_1$ to $C_{20}$ group as defined above, more preferably a $C_2$ to $C_{20}$ alkyl, aryl, alklyaryl, cycloalkyl, or heterocyclic, most preferably a $C_5$ to $C_{20}$ arylalkyl group. It is particularly preferred when R is selected from the $C_9$ to $C_{12}$ arylalkyl, and halogen-containing arylalkyl. R can also be a spacing group like G.

k is an integer that will vary to satisfy the oxidation state of "X" but will range from about 1 to 3. For example, when X is phosphorous k will be an integer from 1 to 3, preferably 2. When X is nitrogen k is equal to 1 and when X is sulfur k is an integer from 0 to 3.

Non-limiting examples of bulky R substituents include:

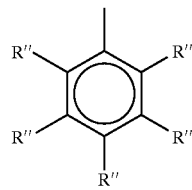
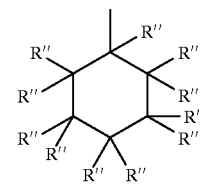
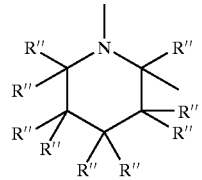
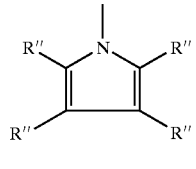
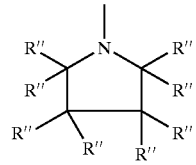
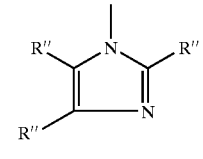
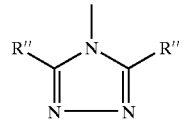
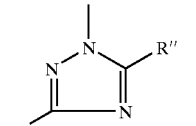
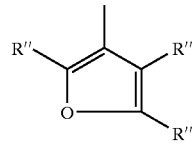
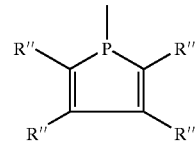

-continued

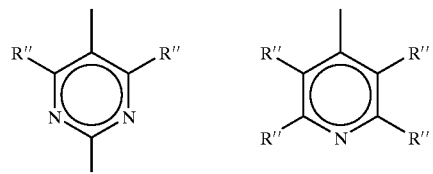
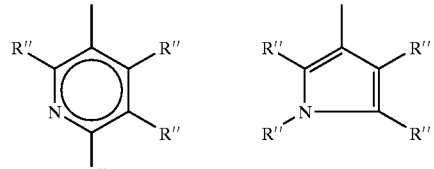
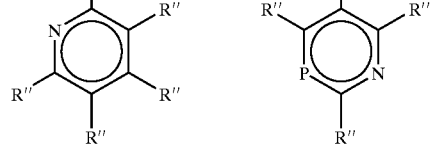
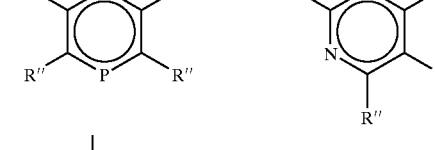
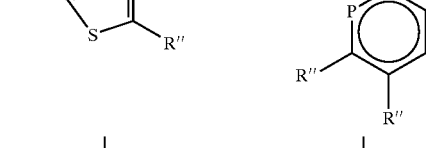
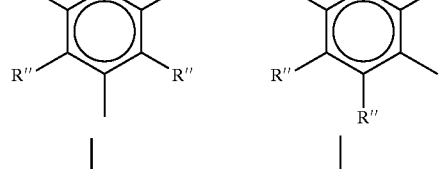
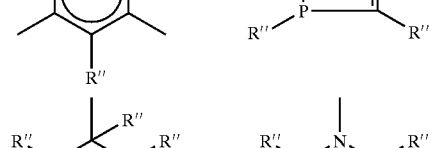
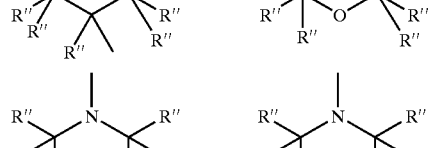

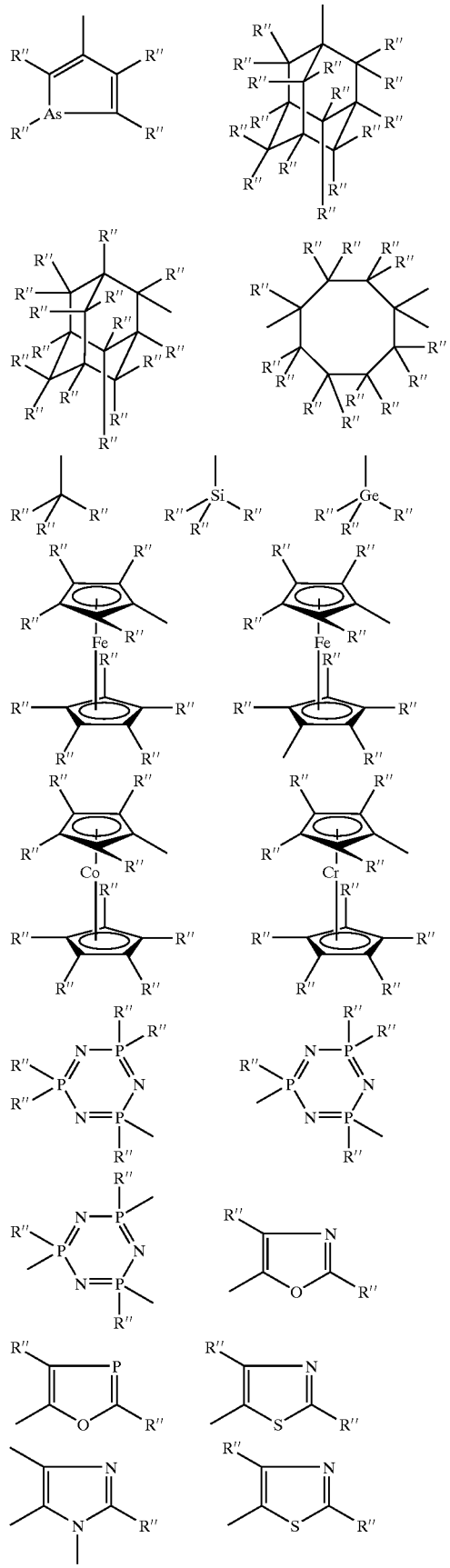

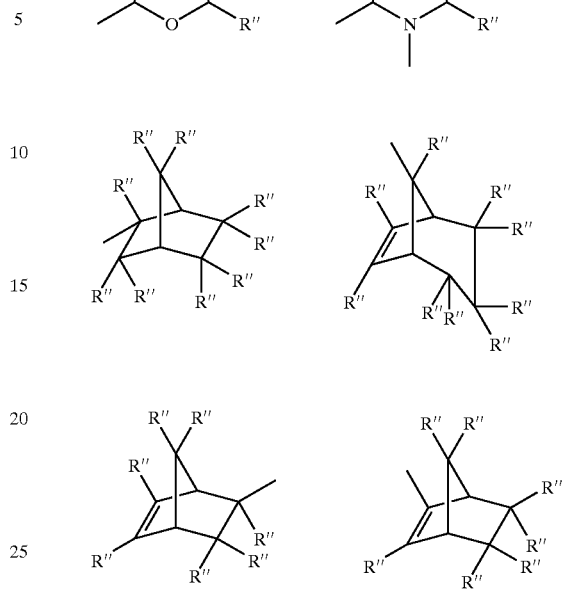

It is preferred that the total number of non-hydrogen atoms for the sum of all R″ groups be up to about 40 atoms. It is also preferred that the R″ be selected from hydrogen, halogen-containing groups, and $C_1$ to $C_{30}$ alkyl, aryl, alkylaryl, arylalkyl, cycloalkyl, and heterocyclic groups as defined above; more preferably R″ is selected from $C_2$ to $C_{20}$ alkyl, aryl, alkylaryl, cycloalkyl, or heterocyclic; and most preferably R″ is a $C_5$ to $C_{20}$ arylalkyl group.

Two or more of X, R, Y, T, and G; preferably X, R, T, and G can be independently co-joined by single, hybridize, or multiple bonds if desired. Representative of co-joined cyclic structures include:

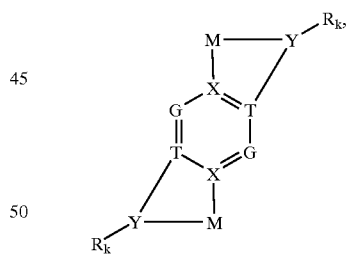

or where t has two or more connecting atoms:

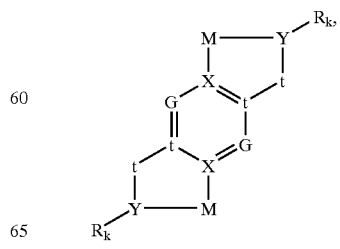

which generic structure can correspond to the composition:

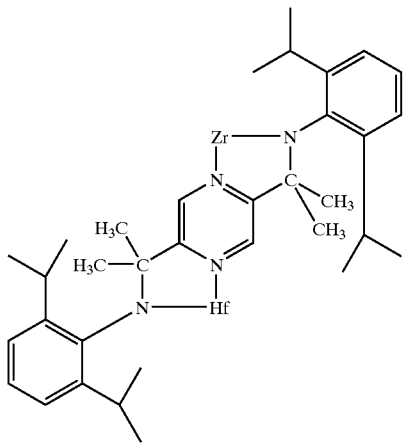

The following represents a structure where T is double bonded to two X moieties.

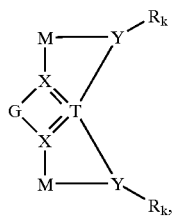

which generic structure can correspond to the composition:

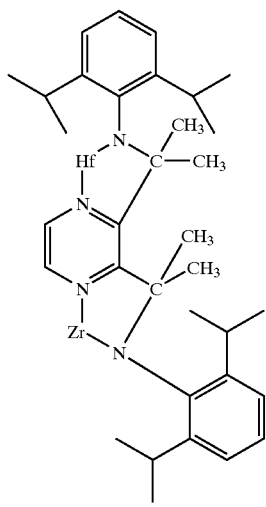

The following generic structure shows T single bonded to one X and double bonded to a second X.

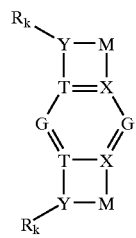

which generic structure can correspond to the composition:

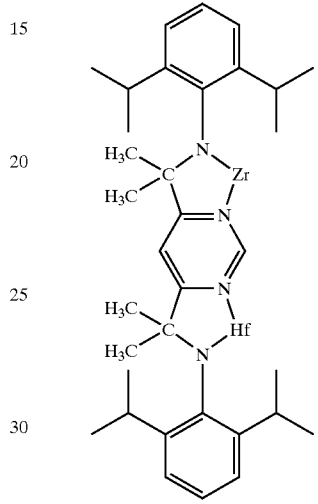

The following is a generic structure show T double bonded to two Xs and G bonded to two Ts.

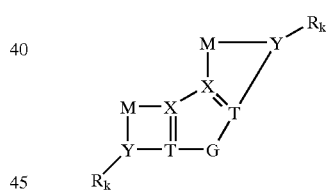

which generic structure can correspond to the composition:

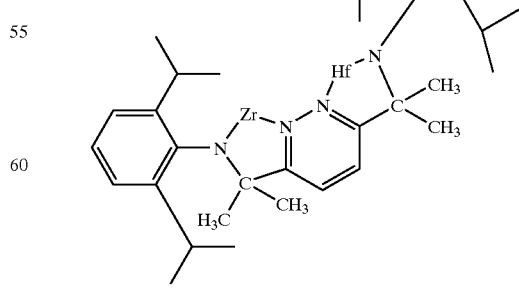

The scope of these structures permits the presence of an X—X bond (shown above).

As long as at least one A is a substituent as defined above at least one of the remaining A substituents is a catalytically active ligand other than that set forth above. This other ligand can be a metallocene ligand or a non-metallocene ligand.

If it is a metallocene ligand it will be a cyclopentadienoid (Cp) family ligand, which includes cyclopentadienyl, substituted cyclopentadienyl, indenyl, fluorenyl, and the like. Such metallocene ligands include: a) the mono Cp complexes wherein: Cp is not tethered with heteroatoms, such as $CpZrX_3$ wherein X is a monoanionic group chloride, alkyl, amine, alkoxide, carboxylate, etc.; and Cp is tethered with heteroatoms to form chelates; b) unbridged bis Cp complexes in which there is no tether between Cp ligands, such as $(Cp)_2ZrX_2$ types; and c) bridged metallocenes which are sometimes referred to as ansa-metallocenes wherein there is a tether "T" between the two Cp moieties, such as $T(Cp)_2ZrX_2$ where T connects the two Cp ligands to form chelates; and d) tri and tetra Cp metallocenes. Non-limiting examples of preferred metallocene ligands include: the dialkyl metallocenes, the mono alkyl metallocenes, the trialkyl metallocenes, the carbene represented by the formula bis (cyclopentadienyl) titanium=$CH_2$ and derivatives thereof, and silicon, phosphine, amine and carbon bridged cyclopentadiene complexes. A more complete list of metallocene ligands that can be used in the practice of this invention can be found in U.S. Pat. No. 5,912,202 which in incorporated herein by reference.

Non-limiting examples of non-metallocene ligands that are suitable for use herein include: imino phenoxides, pyridine bisimines, diazabutadienes, donor bis amides, alkyl ligands such as the simple homoleptic δ-hydrocarbyl complexes of Group 4 transition metals such as $[Ti(CH_2C_6H_5)_4]$ and $[Zr(CH_2C_6H_5)_4]$; allyl ligands; nitrogen-based ligands such as amide ligands; amidinate ligands; oxygen-based ligans, β-diketimate ligands; and the like. A more complete list of such non-metallocene ligands suitable for use herein can be found in a paper entitled *The Search for New-Generation Olefin Polymerization Catalysts: Life beyond Metallocenes*; Britovsek et al.; Angew. Chem. Int. Ed. 1999, 38. pp 428–447, which is incorporated herein by reference.

It is preferred that the A substituent contain from about 1 to 50, more preferably from about 1 to 20 non-hydrogen atoms. Also, one or more of the carbon or hydrogen positions may be substituted with an element other than carbon and hydrogen, preferably an element selected from Groups 14 to 17, more preferably a Group 14 element such as silicon, a group 15 element such as nitrogen, a Group 16 element such as oxygen, or a Group 17 halogen.

G is a spacing group that is capable of bonding to at least two A substituents. G will typically be: organic, including heteroaryl; inorganic; polymeric; or organometallic. G can also inherently possess one or more catalytically active sites. It is preferred that G be alkyl, alkenyl, cycloalkyl, heterocyclic (both heteroalkyl and heteroaryl), alkylaryl, arylalkyl, and polymeric. It is preferred that the G substituent contain from about 1 to 50, more preferably from about 1 to 20 non-hydrogen atoms. Also, one or more of the carbon or hydrogen positions may be substituted with an element other than carbon and hydrogen, preferably an element selected from Groups 14 to 17, more preferably a Group 14 element such as silicon, a group 15 element such as nitrogen, a Group 16 element such as oxygen, or a Group 17 halogen.

The catalyst precursor may be conveniently prepared by reacting an organometallic compound with a heteroatom-containing ligand represented by the formula:

wherein G, g, A, n, M, m, L, and p are as defined above.

In one embodiment of the present invention, when the transition metal is zirconium, a preferred catalyst precursor can be represented by:

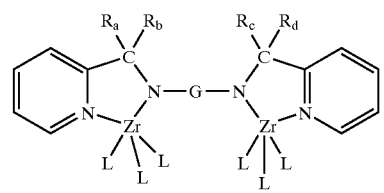

wherein $R_a$, $R_b$, $R_c$, $R_d$ are each independently selected from the group consisting of alkyl, aryl, alkylaryl, alkylaryl, heterocyclic groups, and each L has the meaning stated above.

In another embodiment of the present invention the catalyst precursor can be selected from:

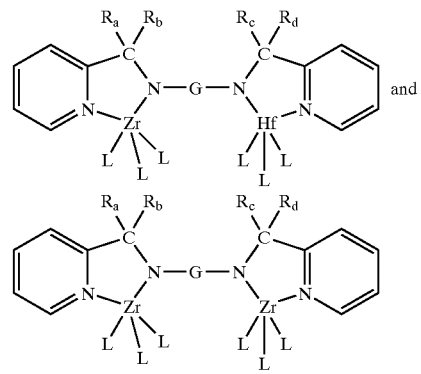

In yet another embodiment of the present invention, the catalyst precursor can be represented by:

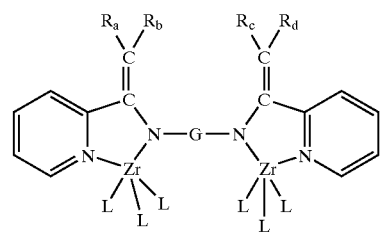

In a further embodiment of the present invention, the catalyst precursor can be represented by:

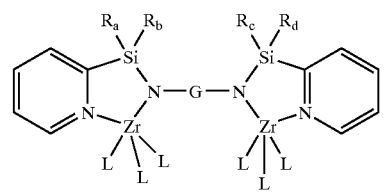

The catalyst precursor may be made by any method. The method of making the catalyst precursor is not critical to the invention. However, one useful method of making the catalyst precursor is by reacting an organometallic compound or a metal halide with a heteroatom-containing ligand represented by the formula:

where A, G, and $A^1$ are as defined above.

A further embodiment of the present invention is represented by the formula below wherein A and $A^1$ are bonded to the G spacing group on the imine nitrogen:

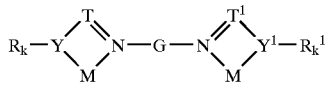

which can correspond to:

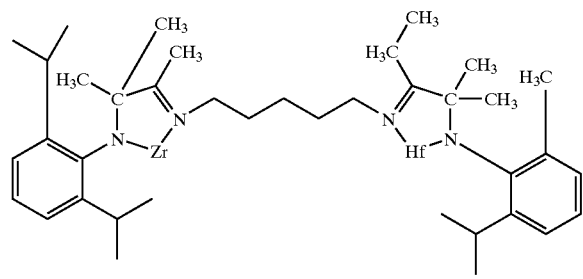

The metal of the organometallic compound may be selected from Groups 3 to 13 elements and Lanthanide series elements. Preferably, the metal is a Group 4 element. More preferably the metal is zirconium.

The catalyst precursors may be prepared by any suitable synthesis method and the method of synthesis is not critical to the present invention. One useful method of preparing the catalyst precursors of the present invention is by reacting a suitable metal compound, preferably one having a displaceable anionic ligand, with a heteroatom-containing ligand of this invention. Non-limiting examples of suitable metal compounds include organometallics, metal halids, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocynates, cyanates, and the metal cyanides. Preferred are the organometallics and the metal halides. More preferred are the organometallics.

As previously mentioned, the metal of the organometal compound may be selected from Groups 1 to 16, preferably it is a transition metal selected from Groups 3 to 13 elements and Lanthanide series elements. It is also preferred that the metal be selected from Groups 3 to 7 elements. It is particularly preferred that the metal be a Group 4 metal, more particularly preferred is zirconium and hafnium, and most particularly preferred is zirconium.

The transition metal compound can, for example, be a metal hydrocarbyl such as a metal alkyl, metal aryl, or metal arylalkyl; metal silylalkyl; metal amide; or metal phosphide. Preferably, the transition metal compound is a zirconium or hafnium hydrocarbyl. More preferably, the transition metal compound is a zirconium arylalkyl. Most preferably, the transition metal compound is tetrabenzylzirconium.

Examples of useful transition metal compounds are tetramethylzirconium, tetraethylzirconium, zirconium-dichloride ($\eta^4$-1,4-diphenyl-1,3-butadiene), bis (triethylphosphine) and zirconiumdichloride ($\eta^4$-1,4-diphenyl-1,3-butadiene) bis (tri-n-propylphosphine), tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium.

Examples of useful transition metal compounds are tetramethyltitanium, tetraethyltitanium, titaniumdichloride ($\eta^4$-1,4-diphenyl-1,3-butadiene), bis (triethylphosphine), titaniumdichloride ($\eta^4$-1,4-diphenyl-1,3-butadiene), bis (tri-n-propylphosphine), tetrakis[trimethylsilylmethyl]-titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium.

Examples of useful transition metal compounds are tetramethylhafnium, tetraethylhafnium, hafniumdichloride ($\eta^4$-1,4-diphenyl-1,3-butadiene), bis (triethylphosphine), hafniumdichloride ($\eta^4$-1,4-diphenyl-1,3-butadiene), bis (tri-n-propylphosphine), tetrakis[trimethylsilylmethyl]hafnium, tetrakis[dimethylamino]hafnium, dichlorodibenzylhafnium, chlorotribenzylhafnium, trichlorobenzylhafnium, bis[dimethylamino]bis[benzyl]hafnium, and tetrabenzylhafnium.

Activators and Activation Methods for Catalyst Compounds

The polymerization catalyst compounds of the invention are typically activated in various ways to yield compounds having a vacant coordination site that will coordinate, insert, and polymerize olefin(s). For the purposes of this patent specification and appended claims, the term "activator" is defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts.

A. Alumoxane and Aluminum Alkyl Activators

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialklylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. Another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum Alkyl or organoaluminum compounds which may be utilized as activators include trimethylaluminum, triethylaluminum, triisobutylaluminum, tri-n-hexylaluminum, tri-n-octylaluminum and the like.

B. Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronapntyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B 1-0 500 944, EP-A-0 277 003 and BP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

In a preferred embodiment, the stoichiometric activators include a cation and an anion component, and may be represented by the following formula:

$$(L-H)_d^+ (A^{d-}) \quad\quad\quad (X)$$

wherein L is an neutral Lewis base;

H is hydrogen;

$(L-H)^+$ is a Bronsted acid;

$A^{d-}$ is a non-coordinating anion having the charge d−;

d is an integer from 1 to 3.

The cation component, $(L-H)_d^+$ may include Bronsted acids such as protons or protonated Lewis bases or reducible Lewis acids capable of protonating or abstracting a moiety, such as an akyl or aryl, from the bulky ligand metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L-H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ wherein k is an integer from 1 to 3; n is an integer from 2–6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Most preferably, the ionic stoichiometric activator $(L-H)_d^+ (A^{d-})$ is N,N-dimethylanilinium tetra (perfluorophenyl)borate or triphenylcarbenium tetra (perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

Supports, Carriers and General Supporting Techniques

The catalyst system of the invention preferably includes a support material or carrier, or a supported activator. For example, the catalyst compound of the invention is deposited on, contacted with, vaporized with, bonded to, or incorporated within, adsorbed or absorbed in, or on, a support or carrier.

A. Support Material

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B 1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200 μm. Most preferably the surface area of the support material is in the range is from about 100 to about 400 m$^2$/g, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

The support materials may be treated chemically, for example with a fluoride compound as described in WO 00/12565, which is herein incorporated by reference. Other supported activators are described in for example WO 00/13792 that refers to supported boron containing solid acid complex.

In a preferred method of forming a supported catalyst composition component, the amount of liquid in which the activator is present is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956).

B. Supported Activators

In one embodiment, the catalyst composition includes a supported activator. Many supported activators are described in various patents and publications which include: U.S. Pat. No. 5,728,855 directed to the forming a supported oligomeric alkylaluminoxane formed by treating a trialkylaluminum with carbon dioxide prior to hydrolysis; U.S. Pat. Nos. 5,831,109 and 5,777,143 discusses a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856,255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of a alumoxane impregnated support and a metallocene and a bulky aluminum alkyl and methylalumoxane; EP-B1-0 662 979 discusses the use of a metallocene with a catalyst support of silica reacted with alumoxane; PCT WO 96/16092 relates to a heated support treated with alumoxane and washing to remove unfixed alumoxane; U.S. Pat. Nos. 4,912,075, 4,937,301, 5,008,228, 5,086,025, 5,147,949, 4,871,705, 5,229,478, 4,935,397, 4,937,217 and 5,057,475, and PCT WO 94/26793 all directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organo-aluminuim compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker, U.S. Pat. Nos. 5,332,706, 5,473,028, 5,602,067 and 5,420,220 discusses a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relates to a process for preparing one or more alkylaluminoxanes immobilized on a solid, particulate inert support; and EP-A1-0 819 706 relates to a process for preparing a solid silica treated with alumoxane. Also, the following articles, also fully incorporated herein by reference for purposes of disclosing useful supported activators and methods for their preparation, include: W. Kaminsky, et al., "Polymerization of Styrene with Supported Half-Sandwich Complexes", Journal of Polymer Science Vol. 37, 2959–2968 (1999) describes a process of adsorbing a methylalumoxane to a support followed by the adsorption of a metallocene; Junting Xu, et al. "Characterization of isotactic polypropylene prepared with dimethylsilyl bis(1-indenyl)zirconium dichloride supported on methylalumi- noxane pretreated silica", European Polymer Journal 35 (1999) 1289–1294, discusses the use of silica treated with methylalumoxane and a metallocene; Stephen O'Brien, et al., "EXAFS analysis of a chiral alkene polymerization catalyst incorporated in the mesoporous silicate MCM-41" Chem. Commun. 1905–1906 (1997) discloses an immobilized alumoxane on a modified mesoporous silica; and F. Bonini, et al., "Propylene Polymerization through Supported Metallocene/MAO Catalysts: Kinetic Analysis and Modeling" Journal of Polymer Science, Vol. 33 2393–2402 (1995) discusses using a methylalumoxane supported silica with a metallocene. Any of the methods discussed in these references are useful for producing the supported activator component utilized in the catalyst composition of the invention and all are incorporated herein by reference.

In another embodiment, the supported activator, such as supported alumoxane, is aged for a period of time prior to use herein. For reference please refer to U.S. Pat. Nos. 5,468,702 and 5,602,217, incorporated herein by reference.

In an embodiment, the supported activator is in a dried state or a solid. In another embodiment, the supported activator is in a substantially dry state or a slurry, preferably in a mineral oil slurry.

In another embodiment, two or more separately supported activators are used, or alternatively, two or more different activators on a single support are used.

In another embodiment, the support material, preferably partially or totally dehydrated support material, preferably 200° C. to 600° C. dehydrated silica, is then contacted with an organoaluminum or alumoxane compound. Preferably in an embodiment where an organoaluminum compound is used, the activator is formed in situ on and in the support material as a result of the reaction of, for example, trimethylaluminum and water.

In another embodiment, Lewis base-containing supports are reacted with a Lewis acidic activator to form a support bonded Lewis acid compound. The Lewis base hydroxyl groups of silica are exemplary of metal/metalloid oxides where this method of bonding to a support occurs. This embodiment is described in U.S. patent application Ser. No. 09/191,922, filed Nov. 13, 1998, which is herein incorporated by reference.

Other embodiments of supporting an activator are described in U.S. Pat. No. 5,427,991, where supported non-coordinating anions derived from trisperfluorophenyl boron are described; U.S. Pat. No. 5,643,847 discusses the reaction of Group 13 Lewis acid compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions; immobilized Group IIIA Lewis acid catalysts suitable for carbocationic polymerizations are described in U.S. Pat. No. 5,288,677; and James C. W. Chien, Jour. Poly. Sci.: Pt A: Poly. Chem, Vol. 29, 1603–1607 (1991), describes the olefin polymerization utility of methylalumoxane (MAO) reacted with silica ($SiO_2$) and metallocenes and describes a covalent bonding of the aluminum atom to the silica through an oxygen atom in the surface hydroxyl groups of the silica.

In a preferred embodiment, a supported activator is formed by preparing in an agitated, and temperature and pressure controlled vessel a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40 to 120° C. and pressures from 5 psia to 20 psia (34.5 to 138 kPa). An inert gas sweep can also be used in assist in removing solvent. Alternate orders of addition, such as slurrying the support material in an appropriate solvent then adding the activator, can be used.

Polymerization Process

The catalyst systems prepared and the method of catalyst system addition described above are suitable for use in any prepolymerization and/or polymerization process over a wide range of temperatures and pressures. The temperatures may be in the range of from −60° C. to about 280° C., preferably from 50° C. to about 200° C., and the pressures employed may be in the range from 1 atmosphere to about 500 atmospheres or higher.

Polymerization processes include solution, gas phase, slurry phase and a high pressure process or a combination thereof. Particularly preferred is a gas phase or slurry phase polymerization of one or more olefins at least one of which is ethylene or propylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1,4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 3 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In an embodiment, the mole ratio of comonomer to ethylene, $C_x/C_2$, where $C_x$ is the amount of comonomer and $C_2$ is the amount of ethylene is between about 0.001 to 0.200 and more preferably between about 0.002 to 0.008.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene catalysts as described in U.S. Pat. Nos. 5,296,434 and 5,278,264, both of which are herein incorporated by reference.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 600 psig (4138 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In a preferred embodiment, the reactor utilized in the present invention is capable of and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series parallel, or combinations thereof. Non-limiting examples of slurry processes include continuous loop or stirred tank processes. Also, other examples of slurry processes are described in U.S. Pat. Nos. 4,613,484 and 5,986,021, which are herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998, 5,589,555 and 5,977,251 and PCT WO 99/32525 and PCT WO 99/40130, which are fully incorporated herein by reference.

A preferred process of the invention is where the process, preferably a slurry or gas phase process is operated in the presence of a bulky ligand metallocene catalyst system of the invention and in the absence of or essentially free of any scavengers, such as triethylaluminum, triethylaluminum triisobutylaluminum and tri-n-hexylaluminum and diethyl aluminum chloride, dibutyl zinc and the like. This preferred process is described in PCT publication WO 96/08520 and U.S. Pat. Nos. 5,712,352 and 5,763,543, which are herein fully incorporated by reference.

In one embodiment of the invention, olefin(s), preferably $C_2$ to $C_{30}$ olefin(s) or alpha-olefin(s), preferably ethylene or propylene or combinations thereof are prepolymerized in the presence of the metallocene catalyst systems of the invention described above prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578 and European publication EP-B-0279 863 and PCT Publication WO 97/44371 all of which are herein fully incorporated by reference.

In one embodiment, toluene is not used in the preparation or polymerization process of this invention.

Polymer Products

The polymers produced by the process of the invention can be used in a wide variety of products and end-use applications. The polymers produced by the process of the invention include linear low-density polyethylene, elastomers, plastomers, high density polyethylenes, medium density polyethylenes, low density polyethylenes, polypropylene and polypropylene copolymers. Also produced are isotatic polymers, such as poly-1-hexene and bimodal polymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to about 30, particularly greater than 2 to about 10, more preferably greater than about 2.2 to less than about 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference.

The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-F) of from 10 to less than 25, more preferably from about 15 to less than 25.

The polymers of the invention in a preferred embodiment have a melt index ratio ($I_{21}/I_2$) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427 incorporated herein by reference.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117, all of which are herein incorporated by reference.

The polymers of the invention may be blended and/or coextruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

The present invention will be illustrated in more detail with reference to the following examples, which should not be construed to be limiting in scope of the present invention.

Glossary

Activity is measured in g of polyethylene/mmol of metal per hr at 100 psig ethylene.

I2 is the flow index (dg/min) as measured by ASTM D-1238-Condition E at 190° C.

I21 is the flow index (dg/min) as measured by ASTM D-1238-Condition F.

MFR is the Melt Flow Ratio, I21/I2.

MMAO is a solution of modified methylalumoxane in heptane, approximately 1.9 molar in aluminum, commercially available from Akzo Chemicals, Inc. (type 3).

BBF is Butyl Branching Frequency, number of butyl branches per 1000 main chain carbon atoms, as determined by infrared measurement techniques.

$M_w$ is Weight Average Molecular Weight, as determined by gel permeation chromatography using crosslinked polystyrene columns; pore size sequence: 1 column less than 1000 Å, 3 columns of mixed $5 \times 10^7$ Å; 1,2,4-trichlorobenzene solvent at 140° C., with refractive index detection. $M_n$ is number average molecular weight.

PDI is the Polydispersity Index, equivalent to Molecular Weight Distribution ($M_w/M_n$).

EXAMPLES

Preparation of Bis an Iminopyridine Ligand

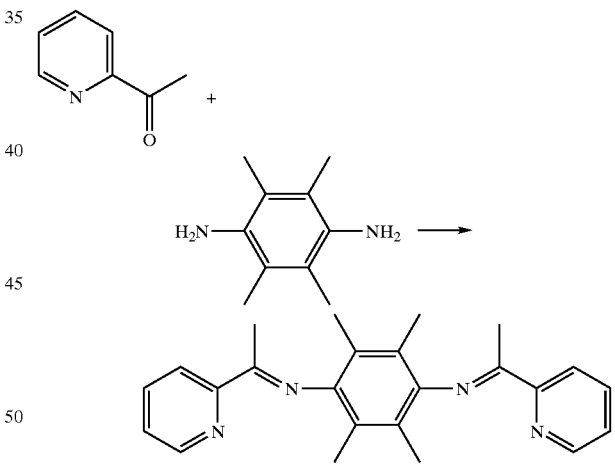

General procedure: Ether (20 mL) and 2-Acetylpyridine (180 mmol, 20 mL) were charged to a 100 mL Schlenk flask equipped with a stir bar. The solution was chilled to 0° C. Hydrochloric acid (2.0 mmol, 1.0M solution in ether) was added. The ice bath was removed and the reaction solution allowed to warm to room temperature. 2,3,5,6-Tetramethyl-1-4-phenylenediamine (30 mmol, 5 g) was added. A Dean-Stark apparatus and cold water condenser were attached to the reaction flask. The reaction was placed under Nitrogen and heated to 180° C. for approximately 6 hours. Heating was discontinued. Hexane was added to the reaction flask and stirred. The green solids were collected by filtration and dried under high vacuum.

Dialkylation of Bis an Iminopyridine Ligand to Bis Aminopyridine Ligand

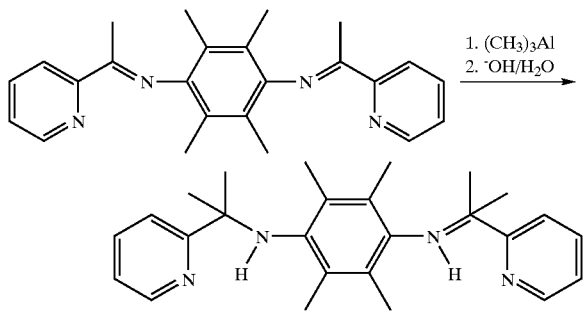

General procedure: Bis Iminopyridine Ligand (2.7 mmol, 1.0 g) was dissolved in 10 mL Toluene in a 25 mL Schlenk flask equipped with a stir bar and septa and chilled to 0° C. Trimethyl aluminum (6 mmol, 3.0 mL, Aldrich, [2.0M soln. in toluene]) was charged dropwise via syringe. The reaction was allowed to slowly warm to room temperature and stir. When complete, the reaction was hydrolyzed with NaOH/ H$_2$O and extracted with ether. The ether extracts were dried over MgSO$_4$ and filtered. The filtrate was vacuum stripped to amber solid residue. Product was confirmed by H-NMR in Benzene-d$_6$.

Reaction of Bis Aminopyridine Ligand with 1 Equivalent of Tetrabenzyl Zirconium

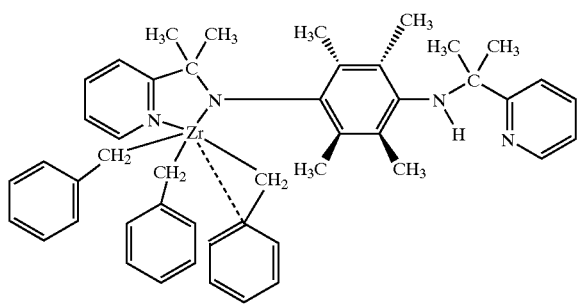

General procedure: In a dry box tetrabenzyl zirconium (0.20 mmol, 0.091 g) was charged to a 7 mL amber bottle equipped with a stir bar and cap. Benzene-d$_6$ (1.5 mL) was added and stirred to dissolve. To a vial was charged bis aminopyridine ligand (0.200 mmol, 0.080 g) and 1.5 mL Benzene-d$_6$. The ligand solution was transferred into the tetrabenzyl zirconium solution.

| MMAO Cocatalyst, Activity | I2 | I21 | MFR | BBF |
|---|---|---|---|---|
| 36,706 | NF | 0.789 | — | 6.95 |

Reaction Conditions: 0.5 micromoles Zr, MMAO/Zr=1,000, 85° C., 85 psi ethylene, 43 mL 1-hexene.

The catalyst most likely becomes a bimetallic Zirconium/ Aluminum-pyridylamide system upon treatment with MMAO)

Reaction of Bis Aminopyridine Ligand with 2 Equivalents of Tetrabenzyl Zirconium

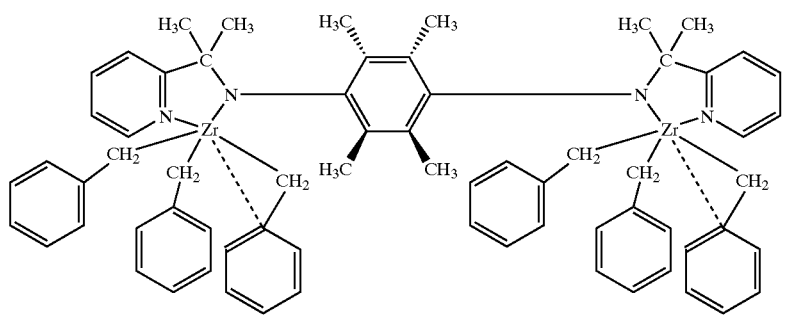

General procedure: In a dry box tetrabenzyl zirconium (0.200 mmol, 0.091 g) was charged to a 7 mL amber bottle equipped with a stir bar and cap. Benzene-d$_6$ (1.5 mL) was added and stirred to dissolve. To a vial was charged Bis Aminopyridine Ligand (0.100 mmol, 0.040 g]) and 1.5 mL Benzene-d$_6$. The ligand solution was transferred into the tetrabenzyl zirconium solution. The reaction was allowed to stir at room temperature overnight.

| MMAO Cocatalyst, Activity | I2 | I21 | MFR | BBF |
|---|---|---|---|---|
| 48,941 | NF | .242 | — | 6.55 |

Reaction Conditions: 0.5 micromoles Zr, MMAO/Zr=1,000, 85° C., 85 psi ethylene, 43 mL 1-hexene.

Reaction of Bis Aminopyridine Ligand with 1 Equivalent of Tetrabenzyl Zirconium and Subsequently 1 Equivalent of Tetrabenzylhafnium General procedure: Analogous to the examples above, the bis aminopyridine ligand was sequentially reacted with one equivalent of tetrabenzylzirconium. After the reaction was complete the resultant compound was reacted with tetrabenzylhafnium. Insoluble solids were formed in this reaction. The solids were isolated and evaluated with MMAO cocatalyst.

| MMAO Cocatalyst, Activity | I2 | I21 | MFR | BBF |
|---|---|---|---|---|
| 19,608 | NF | 0.352 | — | 6.90 |

Reaction Conditions: 0.5 micromoles Zr, MMAO/Zr=1,000, 85° C., 85 psi ethylene, 43 mL 1-hexene.

Reaction of Bis Aminopyridine Ligand with 2 Equivalents of Tetrabenzylhafnium

General procedure: Analogous to the examples above, the bis aminopyridine ligand was reacted with 2 equivalents of tetrabenzylhafnium. Insoluble solids were formed in this reaction. The solids were isolated and evaluated with MMAO cocatalyst.

| MMAO Cocatalyst, Activity | I2 | I21 | MFR | BBF |
|---|---|---|---|---|
| 49,135 | NF | 0.268 | — | 18.18 |

Reaction Conditions: 0.5 micromoles Hf, MMAO/Hf=500, 85° C., 85 psi ethylene, 43 mL 1-hexene.

Reaction of a Lithium Enamide with 6,6-Dimethlyfulvene and then Subsequently Cyclopentadienyl Zirconium Trichloride

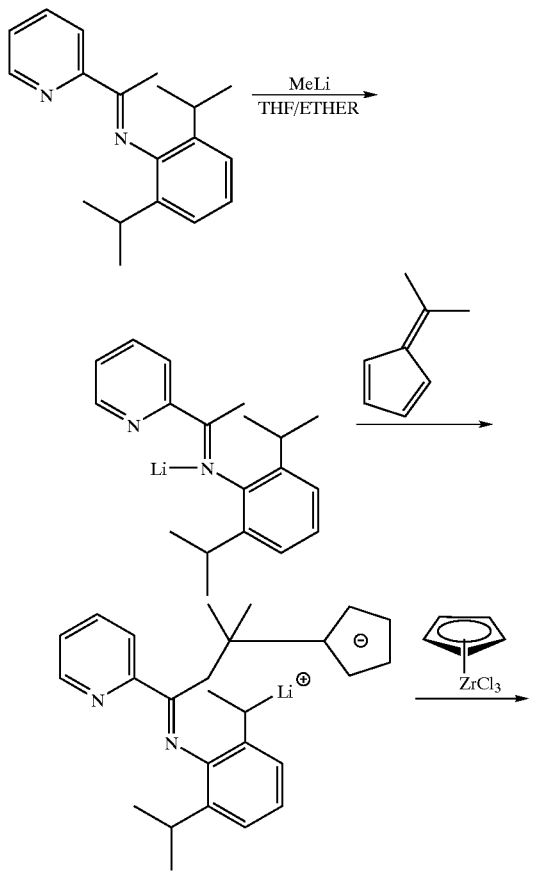

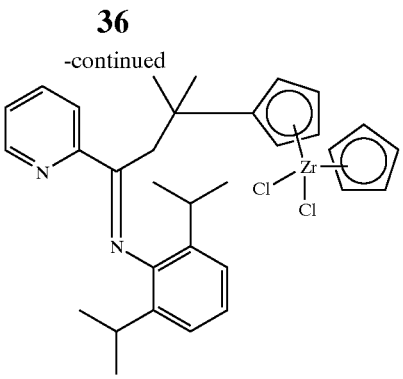

General procedure: The imine precursor above (40 mmol, 11.2 g,) was charged to a 100 mL Schlenk flask equipped with a stir bar and septum. Tetrahydrofuran (20 mL) was added and chilled to 0° C. Methyl lithium (40.0 mmol, 16.0 mL, [1.0 M solution in ether]) was added dropwise to the stirring solution. The reaction solution was allowed to slowly warm to room temperature. After 3 hours cyclopentadienyl zirconiumtrichloride (Aldrich, [40.0 mmol, 10.5 g) was added to the reaction solution. The solution was allowed to stir at room temperature in the dry box over the weekend. The reaction solution was vacuum stripped to a reddish residue. Toluene and hexane were added to the residue and agitated vigorously. The solution was vacuum stripped and additional hexane added with vigorous stirring. The precipitated solids (9.0 g) were collected by filtration, transferred to a 20 mL bottle and stored in the dry box. The filtrate was concentrated and allowed to stand at room temperature in the dry box, yielding a second crop (2.3 g).

Reaction of Zirconocene-Imine Compound with Tetrabenzyl Zirconium

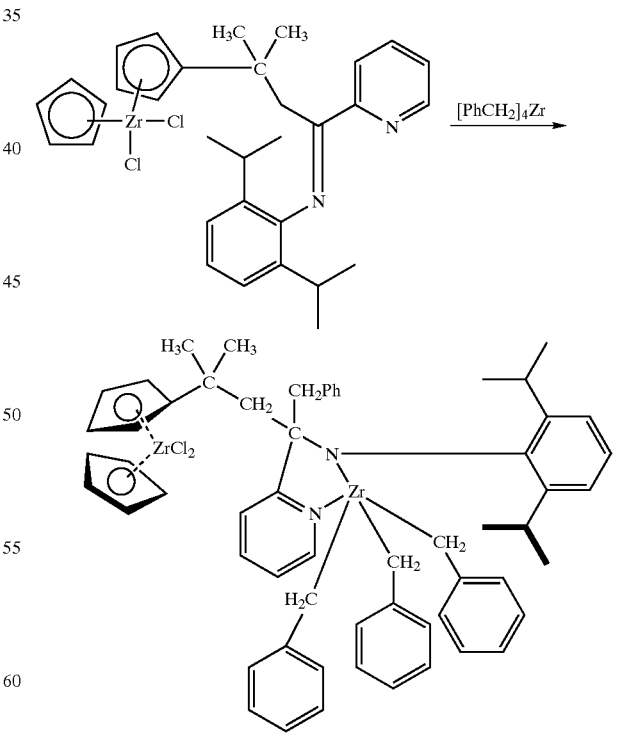

General procedure: In a dry box tetrabenzyl zirconium (0.200 mmol, 0.091 g) was charged to a 7 mL amber bottle equipped with a stir bar and cap. Benzene-$d_6$ (1.5 mL) was added and stirred to dissolve. To a vial was charged zirconocene-imine compound above (0.200 mmol, 0.116 g) and 1.5 mL Benzene-$d_6$. The resultant ligand solution was transferred into the tetrabenzyl zirconium solution. The reaction was allowed to stir at room temperature overnight.

| $H_2$ psi | Activity | I2 | I21 | MFR | BBF |
|---|---|---|---|---|---|
| 0 | 16000 | NF | 0.249 | — | 4.26 |
| 2 | 34,118 | 4.47 | 230 | 51.4 | 8.0 |

Reaction conditions: 0.5 micromoles Zr, MMAO/Zr=1,000, 85° C., 85 psi ethylene, 43 mL 1-hexene.

Size exclusion chromatography analysis results were obtained with and without hydrogen and the resulting plot is shown in the FIGURE hereof. This FIGURE shows polymeric product contribution from both the non-metallocene and the metallocene catalyst and evidences bimodality with hydrogen.

What is claimed is:

1. A catalyst precursor composition represented by the formula:

wherein M is a metal from Groups 1 to 15 and the Lanthanide series of the Periodic Table of the Elements;
g is an integer equal to or greater than 1;
m is an integer equal to or greater than 2;
each L is a monovalent, bivalent, or trivalent anionic ligand;
p is an integer equal to or greater than 1;
n is an integer equal to or greater than 2;
G is at least a divalent spacing group; and
A is selected from the following catalytically active ligands:

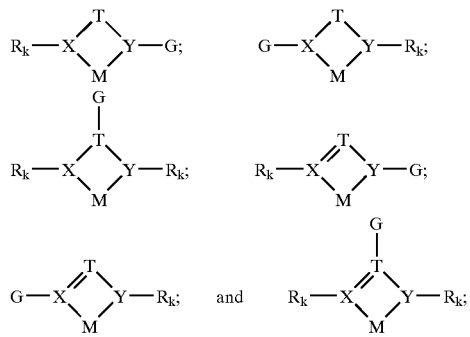

wherein G is bound to at least two substituents;
X and Y are Group 14 or 15 atoms;
T is a bridging group containing 2 or more bridging atoms;
R is selected from bulky and non-bulky substituents with respect to X, Y, or both X and Y, and
k is an integer that will vary to satisfy the oxidation state of but will range from about 1 to 3.

2. The catalyst precursor composition of claim 1 wherein each L is independently a monovalent, bivalent, or trivalent anionic ligand containing from about 1 to 50 non-hydrogen atoms, and is independently selected from the group consisting of halogen containing groups; hydrogen; alkyl; aryl; alkenyl; alkylaryl; arylalkyl; hydrocarboxy; amides, phosphides; sulfides; silyalkyls; diketones; borohydrides; and carboxylates.

3. The catalyst precursor composition of claim 2 wherein each L is independently selected from alkyl, arylalkyl, and halogen containing groups and contains from about 1 to 20 non-hydrogen atoms.

4. The catalyst precursor composition of claim 1 wherein G is selected from alkyl, alkenyl, cycloalkyl, heterocyclic (both heteroalkyl and heteroaryl), alkylaryl, arylalkyl.

5. The catalyst precursor composition of claim 4 wherein G contains from about 1 to 20 non-hydrogen atoms.

6. The catalyst precursor composition of claim 1 wherein G contains from about 1 to 50 non-hydrogen atoms.

7. The catalyst precursor composition of claim 1 wherein R is a non-bulky substituent that has relatively low steric hindrance with resect to X or Y and is selected from the group consisting of straight and branched chain alkyl groups.

8. The catalyst precursor composition of claim 7 wherein R is a $C_1$ to $C_{30}$ alkyl group.

9. The catalyst precursor composition of claim 8 wherein R is a $C_1$ to $C_{20}$ alkyl group.

10. The catalyst precursor composition of claim 1 wherein R is a bulky substituent with respect to X or Y and is selected from alkyl, alkenyl, cycloalkyl, heterocyclic, alkylaryl, and arylalkyl.

11. The catalyst precursor composition of claim 10 wherein R is a bulky substituent and contains 3 to 30 non-hydrogen atoms.

12. The catalyst precursor composition of claim 1 wherein M is selected from Groups 3 to 7 of the Periodic Table of the Elements.

13. The catalyst precursor composition of claim 1 wherein A is represented by:

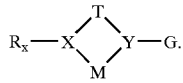

14. The catalyst precursor of claim 1 wherein A is represented by:

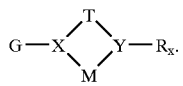

15. A catalyst composition comprising:
a) a catalyst precursor composition represented by the formula:

wherein M is a metal from Groups 1 to 15 and the Lanthanide series of the Periodic Table of the Elements;
g is an integer equal to or greater than 1;
m is an integer equal to or greater than 2;
each L is a monovalent, bivalent, or trivalent anionic ligand;
p is an integer equal to or greater than 1;
n is an integer equal to or greater than 2;
G is at least a divalent spacing group; and
A is selected from the following catalytically active ligands:

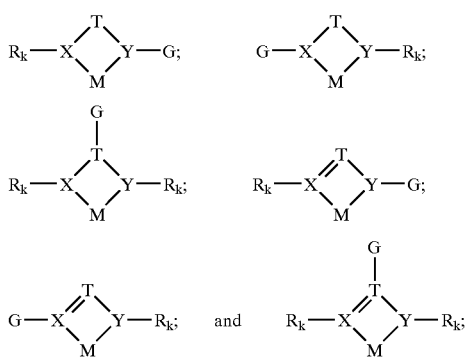

wherein G is bound to at least two A substituents;

X and Y are Group 14 or 15 atoms;

T is a bridging group containing 2 or more bridging atoms;

R is selected from bulky and non-bulky substituents with respect to X, Y, or both X and Y; and k is an integer that will vary to satisfy the oxidation state of but will range from about 1 to 3;

b) and an activator.

16. The catalyst composition of claim 15 wherein T is selected from:

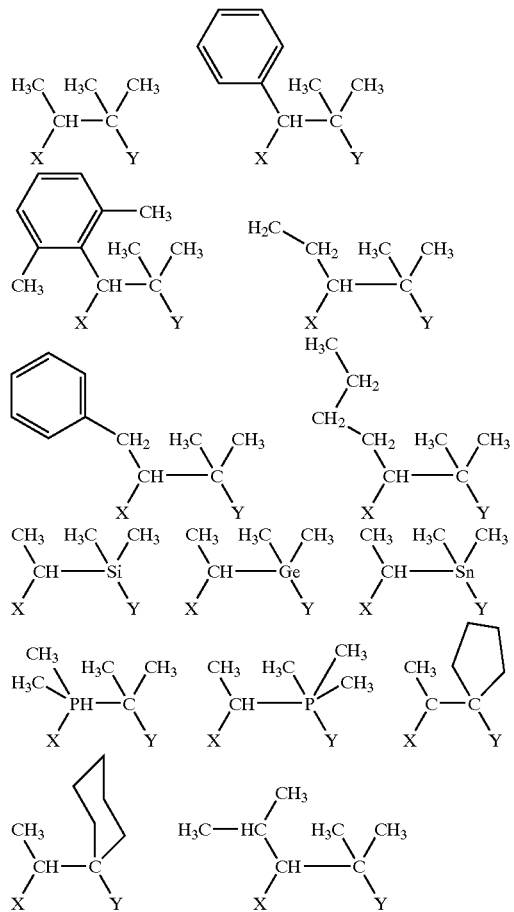
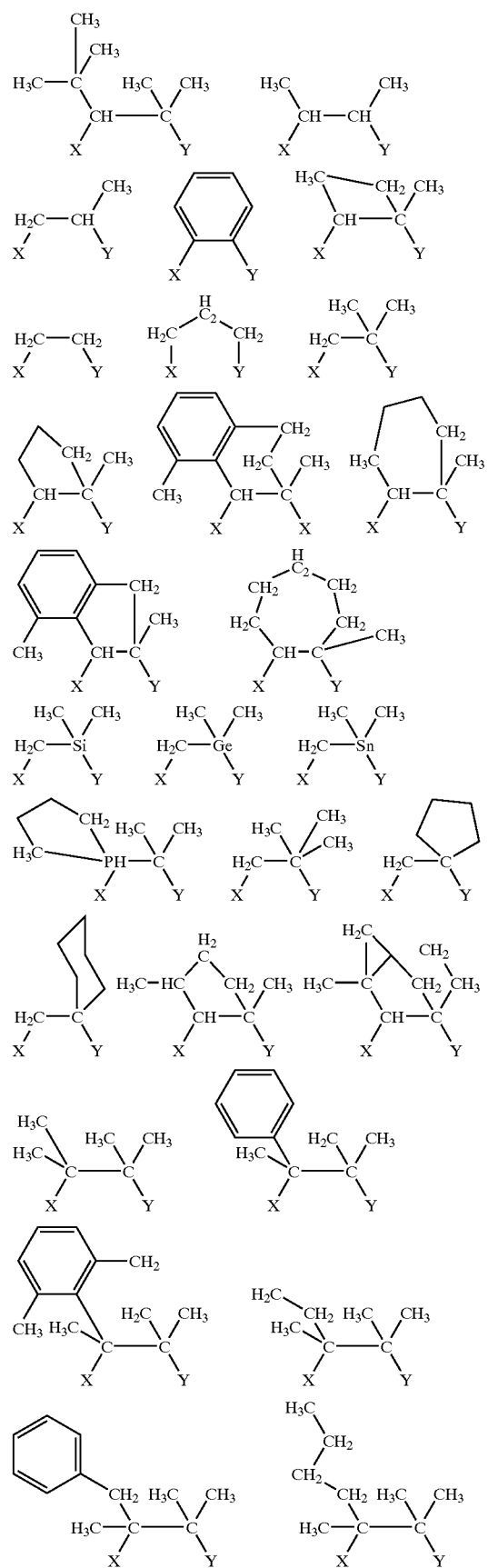

-continued

[chemical structures]

wherein the X and Y substituents are included for convenience.

17. The catalyst composition of claim 15 wherein each L is independently a monovalent, bivalent, or trivalent anionic ligand containing from about 1 to 50 non-hydrogen atoms, and is independently selected from the group consisting of halogen containing groups; hydrogen; alkyl; aryl; alkenyl; alkylaryl; arylalkyl; hydrocarboxy, amides, phosphides; sulfides; silyalkyls; diketones; borohydrides; and carboxylates.

18. The catalyst composition of claim 17 wherein each L is independently selected from alkyl, arylalkyl, and halogen containing groups and contains from about 1 to 20 non-hydrogen atoms.

19. The catalyst composition of claim 15 wherein G is selected from alkyl, alkenyl, cycloalkyl, heterocyclic, alkylaryl, arylalkyl and heteroalkyl.

20. The catalyst composition of claim 19 wherein G contains from about 1 to 50 non-hydrogen atoms.

21. The catalyst composition of claim 15 wherein R is a non-bulky substituent that has relatively low steric hindrance with respect to X or Y and is selected from the group consisting of straight and branched chain alkyl groups.

22. The catalyst composition of claim 21 wherein R is a $C_1$ to $C_{30}$ alkyl group.

23. The catalyst composition of claim 22 wherein R is a $C_1$ to $C_{20}$ alkyl group.

24. The catalyst composition of claim 15 wherein R is a bulky substituent with respect to X or Y and is selected from alkyl, alkenyl, cycloalkyl, heterocyclic, alkylaryl, and arylalkyl.

25. The catalyst composition of claim 24 wherein R is a bulky substituent and contains 3 to 30 non-hydrogen atoms.

26. The catalyst composition of claim 15 wherein M is selected from Groups 3 to 7 of the Periodic Table of the Elements.

27. The catalyst composition of claim 15 wherein A is represented by:

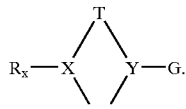

28. The catalyst composition of claim 16 wherein A is represented by:

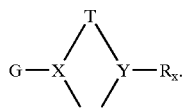

29. The catalyst precursor composition of claim 1, wherein X and Y are selected from nitrogen, sulfur and phosphorous.

30. The catalyst composition of claim 15, wherein X and Y are selected from nitrogen, sulfur and phosphorous.

* * * * *